United States Patent
Mathur et al.

(10) Patent No.: US 12,065,625 B2
(45) Date of Patent: Aug. 20, 2024

(54) METHODS AND FORMULATIONS FOR ENHANCING HIGH VALUE LIPIDS

(71) Applicants: Indian Oil Corporation Limited, Maharashtra (IN); Department of Biotechnology, New Delhi (IN)

(72) Inventors: Anshu Shankar Mathur, Haryana (IN); Preeti Mehta, Haryana (IN); Rekha Rani, Haryana (IN); Ravi Prakash Gupta, Haryana (IN); Suresh Kumar Puri, Haryana (IN); Sankara Sri Venkata Ramakumar, Haryana (IN)

(73) Assignees: Indian Oil Corporation Limited, Mumbai (IN); Department of Biotechnology, New Delhi (IN)

( * ) Notice: Subject to any disclaimer, the term of this patent is extended or adjusted under 35 U.S.C. 154(b) by 0 days.

(21) Appl. No.: 18/083,181

(22) Filed: Dec. 16, 2022

(65) Prior Publication Data
US 2023/0193152 A1    Jun. 22, 2023

(30) Foreign Application Priority Data
Dec. 16, 2021    (IN) .............. 202121058693

(51) Int. Cl.
  C11B 5/00    (2006.01)
  C11B 1/10    (2006.01)
(52) U.S. Cl.
  CPC .............. *C11B 5/0092* (2013.01); *C11B 1/10* (2013.01)

(58) Field of Classification Search
  CPC ..... C11B 5/0092; C11B 1/10; C12R 2001/89; C12N 1/32; C12N 1/12; C12P 7/6427; C12P 7/6472; C12P 7/6434; C12P 7/6463
  See application file for complete search history.

(56) References Cited

U.S. PATENT DOCUMENTS

| | | |
|---|---|---|
| 8,124,384 B2 | 2/2012 | Bailey et al. |
| 9,434,898 B2 | 9/2016 | Raney et al. |
| 9,816,116 B2 | 11/2017 | Comini et al. |
| 9,848,623 B2 | 12/2017 | Bailey et al. |
| 9,890,402 B2 | 2/2018 | Mathur et al. |

(Continued)

OTHER PUBLICATIONS

Wang et al, Marine Drugs, vol. 17, No. 5, 2019, p. 268. (Year: 2019).*

(Continued)

*Primary Examiner* — Deborah D Carr
(74) *Attorney, Agent, or Firm* — Blank Rome LLP

(57) ABSTRACT

The present invention provides a method for the simultaneous enhancement in biomass and lipids containing omega-3-fatty acids of *Thraustochytrid* microalgae in a single step using synergistic effect of chemical mixture in appropriate proportion in production medium. The process discloses enriching the biomass of microalgae with high value lipids by subjecting the microalgal cells in growth medium supplemented with unique combination of chemical modulators and carbon substrates in the presence of nitrogen. The present invention also provides a novel strain *Schizochytrium* sp. (MTCC 5980) for use in continuous aerobic fermentative lipid production process for enhancing high value lipids like Docosahexaenoic acid (DHA), Docasapentaenoic acid (DPA), Eicosapentaenic acid (EPA) and lipids for biodiesel.

11 Claims, 4 Drawing Sheets describes the effect of different concentrations of crude glycerol on lipid and biomass production in control production media by *Schizochytrium* sp. (MTCC 5980).

(56) References Cited

U.S. PATENT DOCUMENTS

| | | | |
|---|---|---|---|
| 10,085,465 | B2 | 10/2018 | Apt et al. |
| 10,351,814 | B2 | 7/2019 | Delaroche et al. |
| 2009/0004715 | A1 | 1/2009 | Trimbur et al. |
| 2011/0047863 | A1 | 3/2011 | Trimbur et al. |
| 2012/0322157 | A1 | 12/2012 | Yohn et al. |
| 2014/0088317 | A1 | 3/2014 | Wen |
| 2016/0122787 | A1 | 5/2016 | Simpson et al. |
| 2016/0281054 | A1 | 9/2016 | Purdue et al. |
| 2016/0298149 | A1 | 10/2016 | Caulier |

OTHER PUBLICATIONS

Ren et al, Korean Journal of Chemical Engineering, vol. 30, No. 4, 2013), pp. 787-789. (Year: 2013).*
Patil et al, Chemical Engeneering Journal, vol. 268, 2015, pp. 187-196. (Year: 2015).*
Ren et al, Bioprocess and Biosystems Engineering, vol. 32, No. 6, 2009, pp. 837-843, (Year: 2009).*
Hu et al., Effects of low-carbohydrate diets versus low-fat diets on metabolic risk factors: a meta-analysis of randomized controlled clinical trials, 2012, pp. 1-2.
Raimondi et al., Imatinib inhibits VEGF-independent angiogenesis by targeting neuropilin 1-dependent ABL 1 activation in endothelial cells, 2014, pp. 1-3.
Yu et al., FlyBase, 2015, pp. 954-962.
Patel et al., "A Liquid-to-Solid Phase Transition of the ALS Protein FUS Accelerated by Disease Mutation", 2015, pp. 1-2.
Liu et al., suspect that may have underestimated dissolved organic nitrogen (N) but overestimated total particulate N in wet deposition in China, 2015, pp. 1-2.
Li et al., Saturated Fats Compared With Unsaturated Fats and Sources of Carbohydrates in Relation to Risk of Coronary Heart Disease: A Prospective Cohort Study, 2015, pp. 1538-1548.
Patil et al., Effect of Non Antibiotic Antimicrobial Curcuma Longa on Helicobacter Pylori Infection, 2015, pp. 1-6.
Abomohra et al., "Effect of different culture media on the growth and lipids of the green microalgae, Scenedesmus obliquus and Micractinium reisseri as a feedstock for biodiesel production", BOTANY, vol. 37, 2016, pp. 190-198.
Ren et al., "Faster R-CNN: Towards Real-Time Object Detection with Region Proposal Networks", 2016, pp. 1-4.
Mehta et al., "Qi Initiative to Increase ROP Screening", Indian Pediatrics, vol. 55, 2018, pp. 1-3.
Sun et al., "Remote sensing assessment of oil spills near a damaged platform in the Gulf of Mexico", Marine Pollution Bulletin, 2018, pp. 141-151.
Aziz et al., "The association of low serum albumin level with severe COVID-19: a systematic review and meta-analysis", Critical Care, vol. 55, 2020, pp. 1-13.
Naduthodi et al., "Synthetic Biology Approaches to Enhance Microalgal Productivity", Article in Plus, 2018, pp. 1-18.
Zhao et al., "A Role for the Respiratory Chain in Regulating Meiosis Initiation in *Saccharomyces cerevisiaey*", 2018, pp. 1181-1194.
Sun et al., "NASA", Projections of temperature-related non-accidental mortality in Nanjing, 2019, pp. 1.
Wang et al., Effects of background complexity on consumer visual processing: An eye-tracking study, 2019, pp. 1-8.
Shahid et al., "Applications of artificial neural networks in health care organizational decision- making: A scoping review", Plos One, 2019, pp. 1-28.
Chen et al., Epidemiological and clinical characteristics of 99 cases of 2019 novel coronavirus pneumonia in Wuhan, China: a descriptive study, 2020, pp. 1-2.
Kujawska et al., Bifidobacterium castoris strains isolated from wild mice show evidence of frequent host switching and diverse carbohydrate metabolism potential, 2021, pp. 1-47.

* cited by examiner

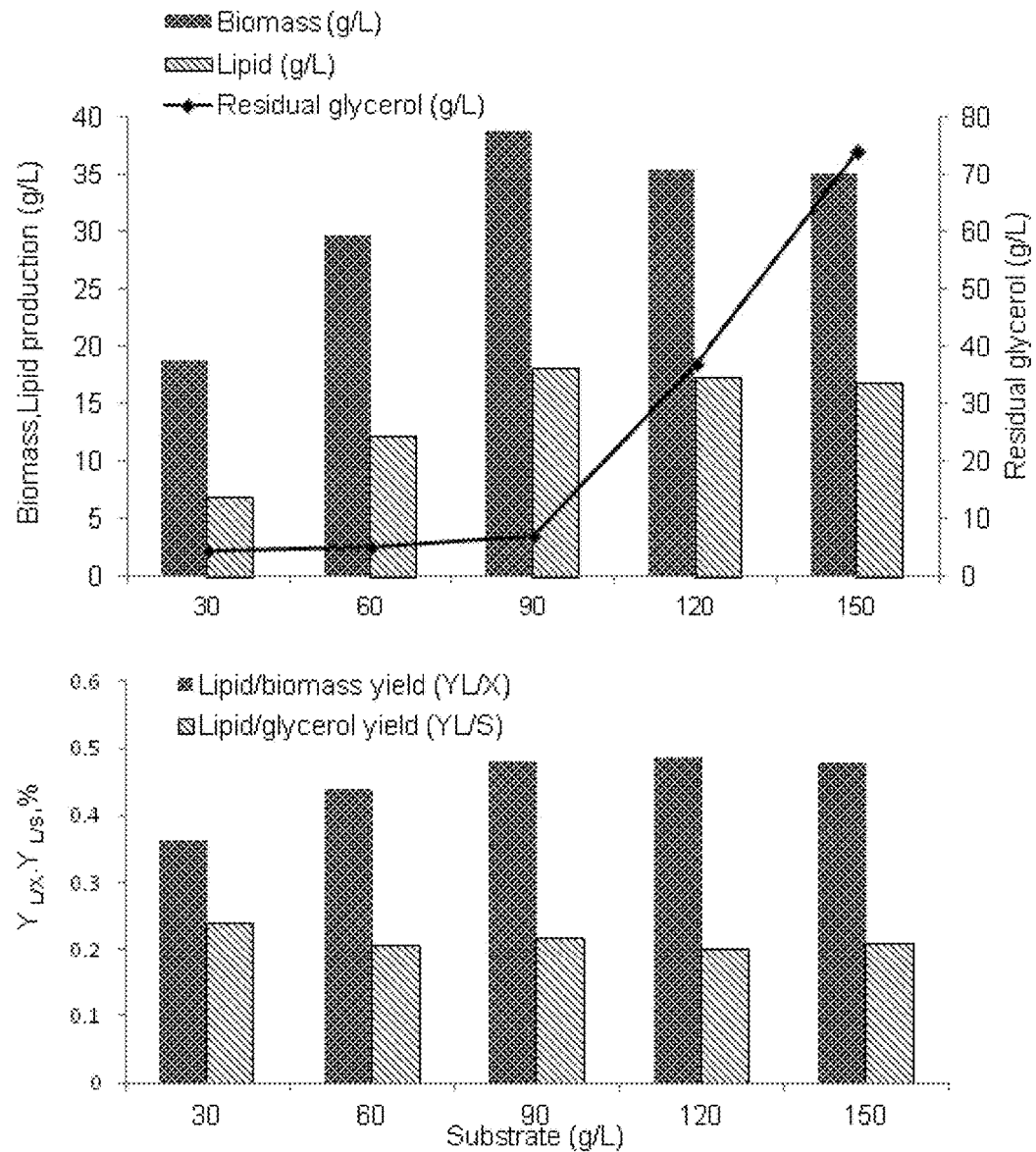
FIGURE 1 describes the effect of different concentrations of crude glycerol on lipid and biomass production in control production media by *Schizochytrium sp. (MTCC 5980)*

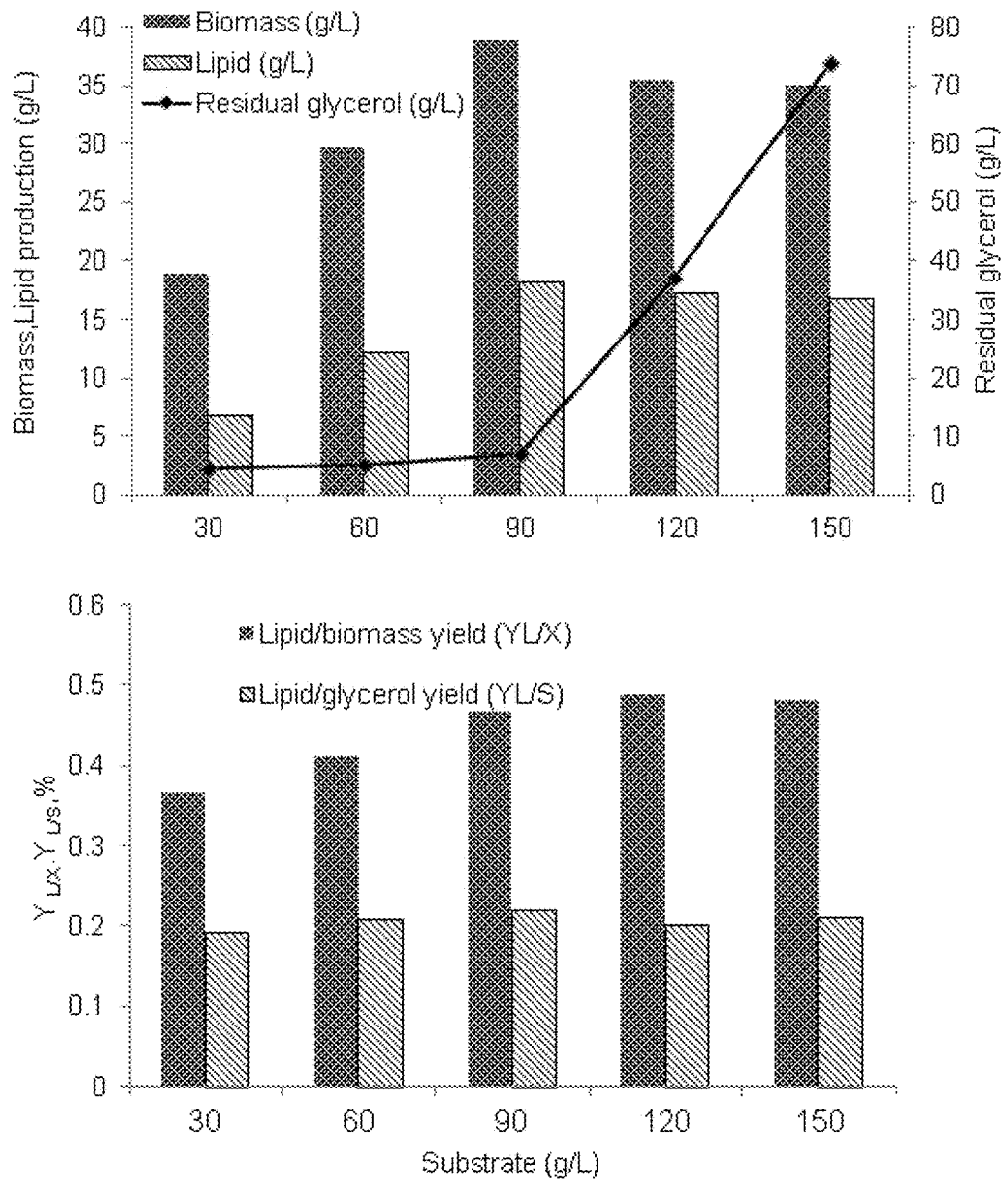
FIGURE 2 describes the effect of different concentrations of pure glycerol on lipid and biomass production in control production media by *Schizochytrium sp. (MTCC 5980)*.

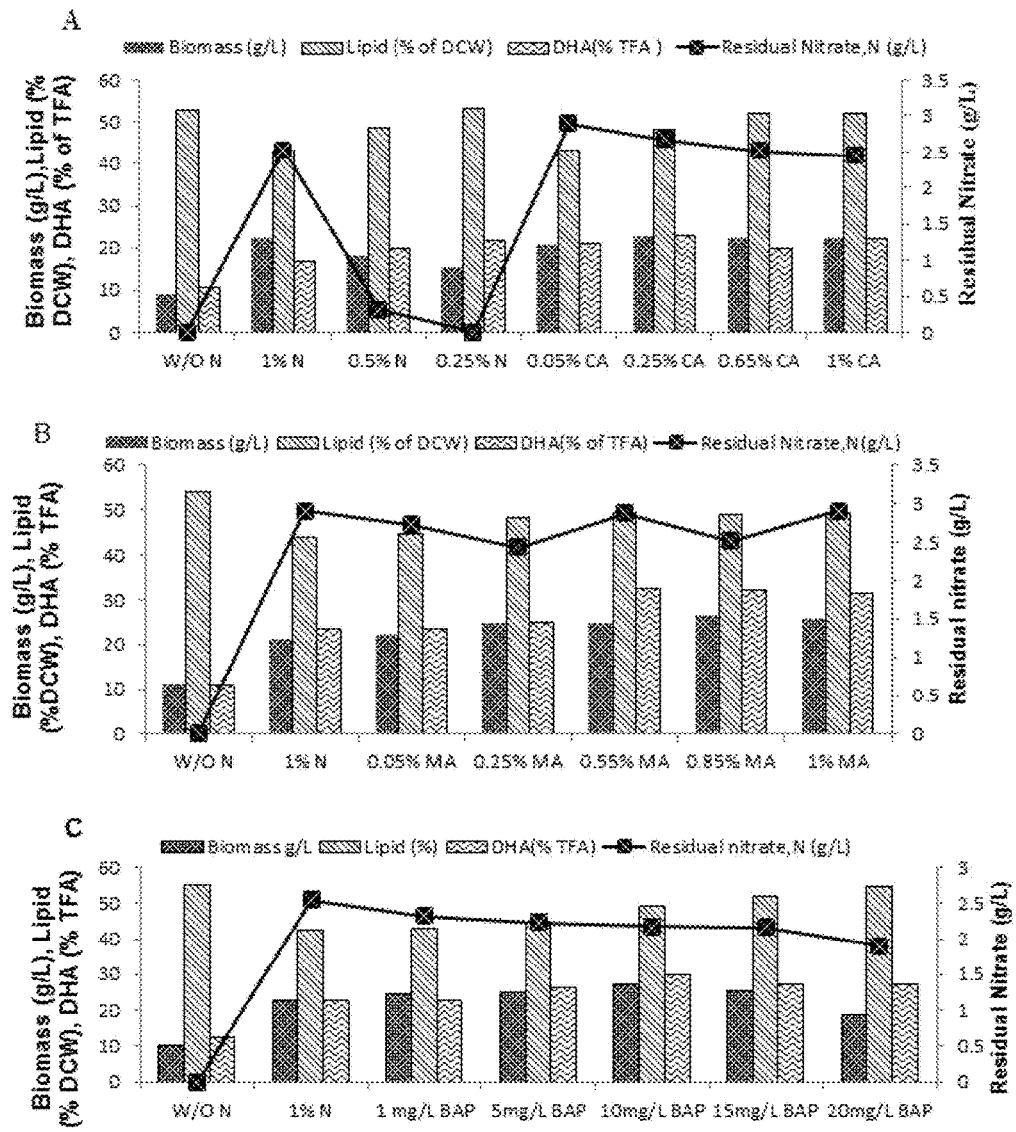
FIGURE 3 describes the effect of different concentrations of modulators; citric acid (A), malic acid (B) and Benzyladenine purines (C) on lipid and biomass production in production media by *Thraustochytrids sp.*

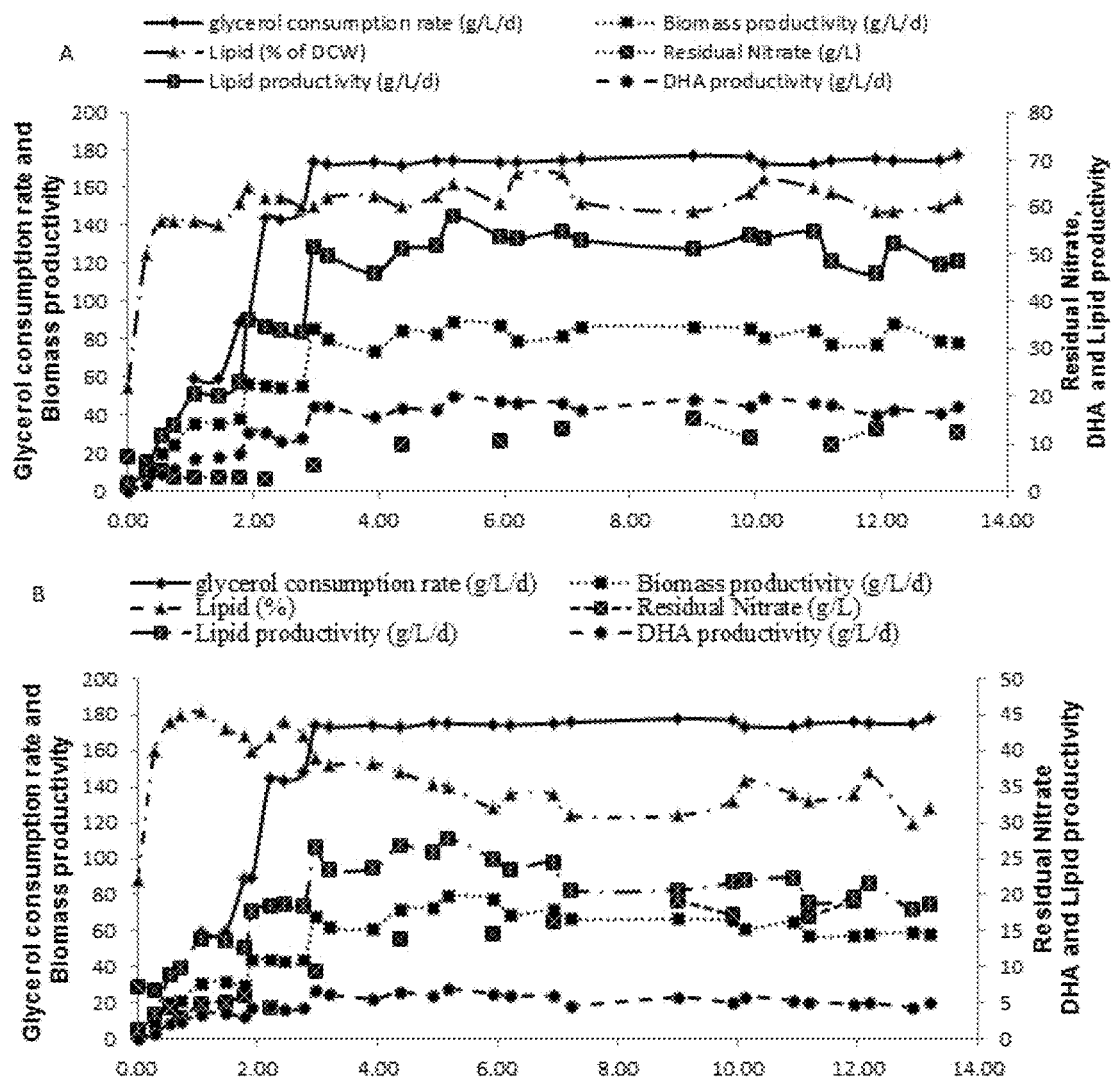
FIGURE 4 describes the changes of biomass, total lipids, DHA productivity in production media containing specific ratio of mixture of modulators (A) and in control (B) in continuous fermentation. Control means no modulators addition

METHODS AND FORMULATIONS FOR ENHANCING HIGH VALUE LIPIDS

RELATED APPLICATION

This application claims the benefit of Indian Application No. 202121058693, filed on Dec. 16, 2021. The entire disclosure of this application is hereby incorporated by reference.

FIELD OF THE INVENTION

The present invention provides for the simultaneous enhancement in biomass and lipids containing omega-3-fatty acids of microalgae in a single step using synergistic effect of chemical mixture in production medium in a single reactor.

BACKGROUND OF THE INVENTION

Due to the ever-increasing demand of energy sources and the ongoing depletion of fossil fuel resources, a major part of research is focused on finding renewable energy-replacement alternatives to petroleum feedstock (Abomohra et al., 2016). In recent years, bio-oil or microbial biomass derived fuel has become a unique platform for research, to counter the negative consequences of harmful emissions raised due to excessive fossil fuel usage in a sustainable manner (Mehta et al., 2018). Most efforts for developing such a platform involve the cultivation of several groups of oleaginous microbes such as green algae, Thrautochytrids and yeast.

Among various oil producing microbes, *Thraustochytrids* are considered as a potential candidate because it is coupled with its modest, innate de novo lipogenesis for the sustainable generation of high value lipids. This organism is unique because they display high cell concentrations and exhibit the noticeable ability to produce lipids droplets for biodiesel along with high value long chain-polyunsaturated fatty acids i.e., docosahexaenoic acid (DHA) and eicosapentaenoic.

Lipid accumulation is obtained in this organism when an essential nutrient, e.g., nitrogen (N), limits cell growth, likewise to the mechanisms for other oleaginous microorganisms (Sun et al., 2018). Microalgae species exhibit two opposing features: high biomass production with low oil accumulation (in nitrogen replete condition), or low biomass production with high oil accumulation (in nitrogen deplete condition). The stressful condition of nutrients for enhancing lipid accumulation may result in the cessation of growth and an overall reduction in lipid productivity. Therefore, the enhancement of the lipid content in oleaginous microbes without decreasing the growth rate is a prerequisite for improving the economic viability of biomass derived biofuel production.

Previous studies mainly focussed on improving the cultivation strategies to enhance the lipid content in microbes by employing the stress-based strategy in different types of fermentation such as: batch, fed-batch, continuous, semi-continuous, and two-stage cultivation strategies (Aziz et al., 2020). These strategies apply the optimum growth conditions at the first stage into maximizing the biomass production and preserve the lipid accumulation in a nutrient-depleted medium at the second stage. US9,848.623B2, U.S. Ser. No. 10/351,814B2, US2016/0298149A1 and U.S. Pat. No. 8,124,384B2 discloses two stage cultivation strategies comprises the oxygen control method i.e., the lower dissolved oxygen during lipid production stage in the absence of nitrogen and high dissolved oxygen during the biomass density increasing stage. The high mixing and aeration for maintaining high dissolved oxygen can easily lead to severe foaming and cells shearing. However, the scalability of these bioprocesses at industrial scale demands more cost and energy. These technologies have reached a point where the lipid productivity of microalgae cannot be further improved using only fermentation optimizations. US publications US2016/0281054A1 and US2014/0088317A1 used crude glycerol as carbon source for the mixture of microalgae and described the fed batch strategies wherein *Thraustochytrid* sp. was cultivated in medium, wherein repetitive feeding of crude glycerol was controlled to maintain threshold concentration level until high cell density was achieved. Two stage continuous systems for production of lipid from gaseous substrate described in US2016/0122787A1. U.S. Pat. No. 9,434,898 B2 discloses the method wherein algal culture was grown in fed batch and the algal biomass was harvested at a negative growth acceleration phase for obtaining high lipid content. However, these patents encompass using the N-stressful condition for lipid production and do not teach the simultaneous production of lipids and high cell density biomass.

In past, some of the known arts suggested homologous recombination or random insertion mutations, molecular modifications of the genes of microalgae, CRISPR-associated transposase technology to improve the quality and quantity of lipids (Shahid et al., 2019). For example, US2011/0047863A1, US2009/0004715A1 discloses methods of genetic modification and expression of hydrocarbon modification enzymes i.e., fatty acyl-ACP thioesterase and fatty acyl-COA/aldehyde reductase in different species of bacterial, yeast and fungus host for high lipid production. US2012/0322157A1 disclosed a method based on stress induced lipid production wherein novel proteins expressed in green algae resulted in an increase or change in fatty acids, without a substantial breakdown of algal components such as chlorophyll. U.S. Pat. No. 10,085,465B2 and U.S. Pat. No. 9,816,116 B2 are directed to the method comprising one or more isolated *Thraustochytrids* and its mutation by site directed and or random and generation of mutants capable of producing high DHA and EPA contents in total lipids. Nevertheless, there are no efficient gene editing methods for all microalgal strains and remains a challenge in most species of microalgae (Naduthodi et al., 2018). Moreover, previous patents disclosed the method of improving the content of total lipid, DHA, DPA in later stage of growth wherein N-stress was stated. Thus, one of the major advances in regulation of lipids and long chain unsaturated fatty acids could be the selection of cost effective efficient chemical additives capable to enhance lipid content in fermentation (Sun et al., 2019).

In recent years, various chemicals molecules (classified as activators and inhibitors) have been identified and are increasingly being used to directly improve the lipid accumulation in cells of microalgae (Sun et al., 2019 and 2018; Yu et al., 2015). In most of the published studies, the effects of chemical molecules like various plant growth hormones, antioxidants, vitamins, organic acids etc (for example fulvic acid, gibberellin, abscisic acid, ascorbic acid, auxin, ethanolamine, EDTA, sesamol, malonate, triethylamine, naphthoxyacetic acid, salicylic acid and jasmonic acid, 6-benzylaminopurine, benzoic acid etc) on lipid accumulation have been investigated (Zhao et al., 2018; Yu et al., 2015). These strategies were successfully applied in batch and fed batch mode and depicted that the total lipid yield increased only at later stages after nitrogen exhaustion (Patel et al., 2015; Aziz et al., 2020). In previous studies, a stepwise strategy was developed to improve both growth and lipid accumulation in microbes in which chemical stimulators added at the first phase for improved biomass productivity and then any stress like nitrogen, salt stress was applied to increase lipid content (Sun et al., 2018). For instance, the lipid yield and docosahexaenoic acid (DHA) productivity was increased by 14.5% and 20.0% in *Schizochytrium* sp. and *Crypthecodinium cohnii* by adding ascorbic acid and sesamol, respectively (Liu et al. 2015; Ren et al. 2016). However, the primary effect of antioxidants was only to reduce oxidative damage, rather than induce lipid biosynthesis itself. Furthermore, a combination of salicylic acid and ETA and naphthoxyacetic acid (BNOA) and ETA supplemented with metals and nitrogen stress increased lipid accumulation by 22.45% in *Crypthecodinium cohnii* (Li et al., 2015). For DHA accumulation in *Schizochytrium* sp, an addition of organic acids to the culture medium at the rapid lipid accumulation stage wherein nitrogen was starved could increase DHA content of total fatty acids from 35 to 60% (Patil et al., 2015). These studies suggested that chemicals are effective at low dosage and their supplementations in medium could improve lipid content unassociated with simultaneous high biomass productivities. This knowledge speaks to the importance of manipulating stressful conditions for enhancing lipid accumulation in concomitant biomass production.

Thus, there is need to enhance oil accumulation and concomitant biomass production from microalgal cells in a single step fermentation uncoupled from any nutrient starvation by employing unique combination of chemical additives. Fatty acid and biomass production rates of microalgae species were compared in nutrient replete/deplete fermentations by supplementing chemical modulators in unique combination in nutrient replete condition only. The culture in appropriate compositions of crude glycerol (by-product of biodiesel industry) and/or any waste streams containing C-source and citric acid/malic acid/BAP supplemented medium can produce high biomass and lipid productivities concomitantly without resorting to any starvation conditions. The methods result in high biomass and oil production due to cumulative synergistic effect of unique ratio of modulators used. Such productivities are higher to what can be achieved as reported in glucose and crude glycerol based fed batch fermentations.

SUMMARY OF THE PRESENT INVENTION

The present invention provides a media supplement composition for enhancing the production of omega-3-fatty acid without compromising the biomass production from a low-cost carbon substrate, said composition comprising 0.01-2% modulators selected from the group comprising of citric acid, malic acid, and benzyl adenine purines.

In a feature of the present invention, the modulators are 0.25-0.65% citric acid, 0.25-1% malic acid, and 0.0005-0.0015% benzyl adenine purines.

In another feature of the present invention, the modulators are 0.1-10 g/L of citric acid, 0.1-12 g/L of malic acid, and 1-15 mg/L of benzyl adenine purines.

In another feature of the present invention, the modulators are citric acid, malic acid and benzyl adenine purines are in ratio 0.4:0.58:0.002.

In a feature of the present invention, the omega-3-fatty acid is docosahexaenoic acid.

In another preferred feature the present invention provides a method for enhancing the production of omega-3-fatty acid without compromising the biomass production from a low-cost carbon substrate, the method comprising steps of:

a. providing a supplement composition comprising 0.01-2% modulators selected from the group comprising of citric acid, malic acid, and benzyl adenine purines to the culture; and b. providing a seed culture comprising *Schizochytrium* sp. (MTCC 5980);

wherein the method does not require induction of nitrogen stress for enhancing the production of omega-3-fatty acid.

In another feature of the present invention, substrate is glycerol, and strain is *Schizochytrium* sp. (MTCC 5980).

In a feature of the present invention, the supplement composition consists of 0.1-10 g/L of citric acid (CA), 0.1-12 g/L of malic acid (MA), and 1-15 mg/L of benzyl adenine purines (BAP).

In yet another feature of the present invention, the supplement composition consists of 0.1-10 g/L of citric acid (CA), 0.1-12 g/L of malic acid (MA), and 1-15 mg/L of benzyl adenine purines (BAP).

In a feature of the present invention, the pH of culture is in range of 5.3-9.5.

Objectives of the Present Invention

The present disclosure relates to a high oil accumulation with concomitant biomass production from microalgal cells in a single step fermentor uncoupled from nutrient starvation.

It is the primary objective of the invention to provide a method for enhancing biomass and high value lipid yield in a single reactor at a same time, which leads to reduction in the capital and operational costs.

It is still another objective of the invention to provide a strain of *Schizochytrium* sp. (MTCC 5980), for enhancing lipid and biomass production.

It is further objective of the present invention to provide a process for significant improvement in high value lipids along with higher biomass in a single process, with supplementation of unique ratio of mixture of chemical modulators in production media, by using inhouse developed novel strain.

It is further objective of the present invention to provide a process for significant improvement in biomass and lipid production, whereby during continuous process of fermentation, the permeate is recycled to get water, and other left-over nutrients, and reuse them in the fermentation to economize the process.

It is further objective of the present invention to provide a method for enhancement of lipid/biomass productivity in a single step without giving any nutrient stress by employing cumulative effect of optimal dosage of additives mixture and low-cost substrates.

Another objective of the present invention is to provide a cost-effective efficient hyper lipid production platform for the conversion of carbon into high value-added omega-3-fatty acids and biofuel products to accomplish a state of economic feasibility.

BRIEF DESCRIPTION OF DRAWINGS

FIG. 1 describes the effect of different concentrations of crude glycerol on lipid and biomass production in control production media by *Schizochytrium* sp. (MTCC 5980).

FIG. 2 describes the effect of different concentrations of pure glycerol on lipid and biomass production in control production media by *Schizochytrium* sp. (MTCC 5980).

FIG. 3 describes the effect of different concentrations of modulators; citric acid (A), malic acid (B) and Benzyladenine purines (C) on lipid and biomass production in production media by *Schizochytrium* sp. (MTCC 5980).

FIG. 4 describes the changes of biomass, total lipids, DHA productivity in production media containing specific ratio of mixture of modulators (A) and in control (B) in continuous fermentation. Control means no modulators addition

DESCRIPTION OF THE INVENTION

The main embodiment of the present invention provides a process comprising continuous fermentation for enhancing lipid and biomass in tandem in a single reactor. The process employs the supplementation of specific amounts of different modulators in mixture, whereby the production of lipids and omega-3-fatty acids i.e., DHA and biomass is enhanced concomitantly. The present invention provides the strategy to overcome the negative effects of stress condition on biomass and high value lipids. The cooperative synergistic effects of combination of modulators in a mixture not only increases the accumulation of lipids rich in DHA, but also enhances the biomass at the same time in a single reactor. In a further preferred embodiment, the present invention provides a process, wherein the nutrients fraction and even water are recovered from the fermentation culture broth and are recycled in the process.

The enhancement of the lipid content in microalgae strains without decreasing the growth rate is a prerequisite for improving the economic viability of microalgae-derived biofuel production. The implementation of the present cultivation strategy increases both lipid accumulation and biomass production concomitantly without any stress condition. The specific productivities of biomass and lipids enriched with high value omega-3-fatty acid i.e., DHA are considerably higher in present invention, employing a novel combination of chemical additives with optimum dosages under nitrogen replete condition as compared to nitrogen starvation condition. Necessity for nitrogen starvation is not universal, and it is possible to produce higher lipid and biomass productivities in a single fermentor at a same point of time without giving any nitrogen stress to microbes. The present inventions strategy is found to enhance the biomass and lipid productivity in all the test organisms and any desirable nutrient combinations.

The process includes the steps whereby microalgal strain is *Thraustochytrid* i.e., *Schizochytrium* sp. (MTCC 5980), is cultivated in a medium comprising of low-cost carbon substrates/any waste streams and chemical stimulators as the energy source in fermentation for the enhanced simultaneous production of high cell density biomass and lipids in a single step without any nitrogen stress. Both carbon substrate and chemical modulators are mixed in unique and novel proportions to get medium of adequate pH, thus obviating need of adding acid and base for obtaining optimum pH for microalgal growth.

The present invention relates to a method to produce lipid rich biomass containing a variety of omega-3-fatty acids using crude waste glycerol without pre-treatment as a substrate for algal growth. The method comprising the steps of: (a) providing crude glycerol as culture medium; and (b) culturing of species of *Schizochytrium*, in the crude glycerol culture medium under conditions that permit microalgal species to produce high lipid containing biomass enriched with omega-3 fatty acids such as DHA, EPA etc.

Example In yet another aspect of the present invention it has been found that that novel *thraustochytrid* strain i.e., *Schizochytrium* sp (MTCC 5980) have unique and unexpected property of thriving in high concentration of untreated crude glycerol both in presence and absence of nitrogen source. It was found in the present invention that lacking adequate nitrogen supply triggered high lipid accumulation and less biomass production in the *Schizochytrium* sp. (MTCC 5980). This enabled to adapt various strategies for use of novel *Schizochytrium* sp. (MTCC 5980) in simultaneous production of biomass, lipid and DHA in a single reactor without nitrogen starvation, for example amendment of different combinations of chemical modulators at particular time of fermentation, increased dilution rate and adaptation of the selected strain on these high concentration crude glycerol medium amended with chemical modulators were applied to enhance biomass, lipid and DHA production uncoupled with nitrogen starvation. Moreover, such a unique property of novel *Schizochytrium* sp. (MTCC 5980) enabled the applicants to develop and arrive at unique and novel method comprising of a continuous fermentation for concomitant production of higher biomass, lipids for biodiesel and high value DHA in a single reactor by sequestration of nutrients from waste effluent of biodiesel industries i.e., crude glyecrol.

Example 1

Characterization of Crude Glycerol

Two crude glycerol samples (CG-1 and CG-2) provided by biodiesel manufacturing companies in India. Glycerol samples characterized in order to determine their content of glycerol and other impurities such as methanol, organic fractions (FAME) soaps and residual elements. The density of crude glycerol was determined by measuring the volume and weight of crude glycerol at room temperature ($25\pm0.5°$ C.). For pH determination, crude glycerol (1.00 g) was dissolved in 50 mL of deionized (DI) water. The pH of the solution was measured by a digital pH meter at room temperature ($25\pm0.5°$ C.). Elements including Na, Mg, Al, P, K, Ca, Mn, Fe, Co, Cu, and Zn were determined by ICP-MS (Agilent Technologies ICP-MS 7500 series, Santa Clara, CA). The soap content of crude glycerol was determined with reference to AOCS Recommended Practice Cc 17-9532 and ASTM D 4662-08 (Hu et al., 2012). The glycerol contents of crude glycerol were determined by HPLC (Waters Corp. USA) equipped with an Aminex HPX-87H column (Bio-Rad Laboratories, USA), following the same operating conditions, as described previously (Singh et al., 2017). The methanol concentration of the samples was analysed by a YL6500 Gas Chromatograph (YL instruments, Korea) equipped with a Zebron ZB-Bioethanol column (Phenomenex, 356385, 30 m×0.25 mm, 1.00 μm thickness). The injector was maintained at 250° C. and a sample volume of 1 μL was injected with a 50:1 split ratio. Helium was used as the carrier gas and its flow rate was maintained at 1.5 mL/min. The oven was programmed from 140° C. (5 min hold) to 240° C. (10 min hold) at a rate of 4° C. per min. 2-propanol was used as internal standard. Methanol peaks were identified using system inbuilt chromatography software on comparison with retention times of standards. An external calibration curve was constructed by analysing standard glycerol and methanol solutions at different concentration levels. The compositions of the organic fractions were determined in terms of their FFA, FAME by gas chromatography (GC) using a Perkin Elmer clarus680 GC system (Perkin Elmer clarus680, US) equipped with a flame ionization detector (FID) and fast-GC capillary column (Omegawax100, 15 m×0.1 mm, 0.1 μm thickness) following the protocol described by Mehta et al., 2018.

Chemical composition of crude glycerol before considering value-added conversions, the characterization of crude glycerol was performed and listed in Table 1. The densities of two crude glycerol samples i.e., CG1 and CG2 are 1.12 and 1.10 g/cm³ respectively, lower than that of pure glycerol (1.31 g/cm³), due to the presence of some lighter impurities such as methanol, water, organic fractions etc. fatty in crude glycerol. CG-1 and CG-2 had pH values close to 7.5 because of the existence of some of the residual alkalis left from the biodiesel production process. The free glycerol contents of CG-1 and CG-2 determined by HPLC are 76 and 78%, respectively, which were comparable higher than the glycerol contents reported in previous reports (Hu et al., 2012). On contrary to previous study (Chen et al., 2020), the residual methanol contents in crude glycerol were less, varied between 5 to 7%. The variation in glycerol content and methanol content most likely caused by the various biodiesel production processes and post recovery efficiencies in different biodiesel plants.

Ion contents in crude glycerols were also determined with ICP analysis. Large amount of sodium ion was found because of NaOH was utilized as catalyst. Other cations such as potassium, calcium, iron ion also detected but no trace metal and heavy metal element were found, which indicated that the crude glycerol can be processed for further applications without any safety issues. The fatty acid compositions were analysed which as well indicated a very small portion of organic fraction in the form of Palmitic acid (C16:0), oleic acid (C18:1) and linoleic acid (C18:2).

TABLE 1

Table 1 describes the characteristics, composition, and ion analysis of crude glycerol

| Characteristics | Pure glycerol | Crude glycerol (CG-1) | Crude glycerol (CG-2) |
|---|---|---|---|
| Appearance | Transparent | Deep brown, gel like | Deep brown, gel like |
| Density | 1.32 ± 0.01 | 1.12 ± 0.02 | 1.11 ± 0.01 |
| pH | 6.5 ± 0.0 | 7.5 ± 0.0 | 7.3 ± 0.0 |
| Glycerol (wt %) | 99.5 | 76 ± 0.03 | 78 ± 0.9 |
| Methanol (wt %) | — | 5 ± 1.2 | 7 ± 0.45 |
| Water (wt %) | — | 7.3 ± 0.1 | 8.7 ± 0.11 |
| Soap (wt %) | — | BDL* | BDL* |
| Organic fraction (wt %) | — | 6.5 | 7.2 |
| Al (ppm) | — | 28 ± 0.2 | <5 ± 0.4 |
| Ba (ppm) | — | 8 ± 0.1 | <5 ± 0.1 |
| Ca (ppm) | — | 260 ± 2.5 | <5 ± 0.98 |
| Co (ppm) | — | <5 ± 0.78 | <5 ± 1.76 |
| Cr (ppm) | — | 23 ± 3.7 | <5 ± 4.8 |
| Cu (ppm) | — | <5 ± 1.65 | <5 ± 3.62 |
| Fe (ppm) | — | 1873 ± 16.8 | 228 ± 5.76 |
| K (ppm) | — | 4.1 ± 2.76 | <5 ± 0.98 |
| Li (ppm) | — | <5 ± 1.7 | <5 ± 0.7 |
| Mg (ppm) | — | 134 ± 6.8 | 112 ± 4.87 |
| Mn (ppm) | — | 46 ± 8.8 | 32 ± 9.6 |
| Mo (ppm) | — | <5 ± 2.87 | <5 ± 2.12 |
| Na (ppm) | — | 9265 ± 34.8 | 5187 ± 41.76 |
| Ni (ppm) | — | 13 ± 6.5 | <5 ± 3.1 |
| Ti (ppm) | — | <5 ± 2.76 | <5 ± 1.20 |
| V (ppm) | — | <5 ± 0.98 | <5 ± 3.87 |
| Zn (ppm) | — | 20 ± 4.10 | <5 ± 2.19 |

Example 2

Effect of Crude Glycerol Concentration on Growth and Lipid Accumulation

Preparation of seeding culture and lipid production in shake flask: *Schizochytrium* sp. (MTCC 5980) used in the present invention are isolated from Indian marine sites in March 2013 over 30-35 km stretch in mangrove areas of Ribandar across Mandovi-Zuari mangroves (Mathur et al., 2016). The strain was genetically characterised by 18S sequencing, and the resulting sequences were deposited in NCBI database (with accession no. KF668624). *Schizochytrium* sp. (MTCC 5980) was deposited at Microbial Type Culture Collection and Gene Bank (MTCC) Institute of Microbial Technology (IMTECH), Chandigarh, India.

The defined production medium (GM) used contained 60 g/L crude glycerol (specified elsewhere), 10 g/L $NaNO_3$, 1 g/L peptone, 2.2 g/L $KH_2PO_4$, 2.0 g/L $MgSO_4 \cdot 7H_2O$ and 9 g/L Sea salt and had an initial pH of 7.5. The effect of crude glycerol concentration on growth and lipid production by selected isolates, shake flask cultivation was carried out in the production medium supplemented with different crude glycerol concentrations of 30-120 g/L. A 48 hours culture of *Schizochytrium* sp. (MTCC 5980) in YPD (3% glucose, 0.1% peptone, 1% yeast extract and 18 g/L sea salt) medium was used as inoculum, from which about $10^{10}$ cells (10% (v/v) of defined medium) were inoculated in different conical flasks containing defined media with different concentrations of crude glycerol as above mentioned. The flasks were incubated in a shaker incubator under the following conditions: shaker speed 200 rpm, temperature 30°-35° C. Biomass was harvested and lipid content was analysed after 72 h. The lipid/biomass yield (YL/X) calculated as the grams of lipid produced per gram of biomass and corresponded to the lipid content of biomass. The lipid/glycerol yield (YL/S) calculated as the grams of lipid produced per grams of glycerol consumed.

The effect of crude glycerol concentration on growth and lipid accumulation of *Schizochytrium* MTCC 5980 strain investigated by the addition of crude glycerol at different concentrations in the range of 30-120 g/L to the production medium. With different initial concentrations of glycerol, it is observed that there was variation in the growth and lipid production of the *Schizochytrium* sp. (MTCC 5980) (FIGS. 1 and 2). Increase in the initial glycerol concentration caused increase in the biomass and lipid yield. However, the highest biomass productivity of 7.78 g/L/day was achieved at glycerol concentration of 90 g/L with biomass production and biomass yield of 38.9 g/L and 0.45 g/g glycerol, respectively. Lipid production occurred with a rate of 3.63 g/L/day with a lipid/glycerol yield (YL/S) of 20% as shown in FIG. 1(a) and Table 1. The considerable glycerol conversion into lipids (20 and 23%) was observed in the present disclosure, which is in close agreement with previous study, showing that the maximum theoretical lipid yield from glycerol is approx. 30% w/w and a relevant amount of the carbon flux is drained into storage carbohydrates.

When the culture was cultivated in the media containing higher concentrations of crude glycerol (>90 g/L), slight decrease in growth and lipid production was observed. As a result, the lower cell biomass and lipid concentration (35.12±1.0 and 16.8±0.4 g/L, respectively) were obtained when *Schizochytrium* sp. (MTCC 5980) was cultivated in the medium containing 150 g/L crude glycerol. Despite the greater amount of lipids produced, the volumetric productivity was lower (3.3 g/L/day) at conc. 150 g/L as compared to 90 g/L glycerol concentration (3.63 g/L/day), because glycerol consumption rate progressively decreased, causing the production rate to decline as well (FIG. 1). The highest amount of intracellular lipids was produced by strain *Schizochytrium* sp. (MTCC 5980) at glycerol concentration of 90 g/L followed by 120 g/L and 150 g/L, which yielded 17.4 g/L, 14.8 g/L, 14.4 g/L intracellular lipids, corresponding to 46.7, 48.8, and 47.9% of dry biomass, respectively. Increase in Lipid/biomass yield (YL/X) with higher conc. of carbon indicating that higher amount of the carbon flow was directed toward the synthesis of storage lipid (FIG. 1).

The crude glycerol was almost exhausted in the medium at the end of cultivation for 120 h when added in the range of 30-90 g/L. When crude glycerol was added to the medium at a higher concentration>90 g/L, it was not completely consumed by the strain Schizochytrium sp. (MTCC 5980), particularly, at 120 and 150 g/L crude glycerol; only 66.5% and 50.1%, respectively, were consumed. These results are consistent with previous studies (Chen et al., 2020; Patil et al., 2015) implying that there might still be an osmotic stress for cell metabolic activities at high concentration of crude glycerol, due to which slight decrease in biomass was observed. Moreover, a high concentration of crude glycerol increases the viscosity of the medium, which influenced the mass transfer by limiting the concentration of dissolved oxygen. Therefore, the culture took a longer time to adapt to the medium containing high glycerol concentration.

To handle a reproducible and controllable cultural medium, pure glycerol was used as control to know any potential effect of the impurities occurring in crude glycerol. The results showed that no significant differences were observed between the consumption profiles of pure and crude glycerol at all given concentrations (FIG. 2). Surprisingly, in Schizochytrium sp. (MTCC 5980) crude glycerol consumption was markedly faster than that of pure glycerol (~17.36 and ~16.44 g $L^{-1}$ day$^{-1}$ on crude and pure glycerol, respectively), giving the dry cell weight on crude and pure glycerol was in the range of 18-35 g$L^{-1}$ and 16-32 g$L^{-1}$, respectively, at different concentrations after 120 hours. Lipid productivity (1.3-3.0 g $L^{-1}$ h$^{-1}$) on crude glycerol was close to the one obtained with pure glycerol (1.1-2.9 g $L^{-1}$ day$^{-1}$), and almost the same lipid content (47.9 and 47.01% on crude and pure glycerol, respectively) were obtained. The nutrients, salts and other organic compounds present in crude glycerol enhanced the biomass and lipid productivities as compared to pure glycerol and these findings are in line with previous reports (Raimondi et al., 2014).

Example 3

Lipogenic Induction Through the Optimized Ratios of Different Chemical Modulators The lipid accumulation and DHA enhancement response towards media formulation by cultivation in varying concentrations of citric acid; CA (between 0.1-10 g/L), malic acid; MA (0.1-12 g/L) and Benzyl adenine purines; BAP (1-15 mg/L) in the presence of nitrogen. The medium without nitrogen addition was kept as control. However, glycerol conc. was used at same concentration as discussed in experiments of example 2. Batch experiments were carried out in a parallel bioreactor (Biojenik Engineering, Chennai, India) with 2 L of supplemented GM medium, inoculated 10% v/v with a 24-hours seed culture grown in GM containing 6 g/L glycerol. The culture was kept at 35° C. and aerated with 0.75-1 v/v/min air; stirring was regulated in the range from 150 to 900 rpm to keep the Dissolve oxygen at 20%. The medium pH, incubation temperature, time and agitation were 5.3-9.5, 35° C., 24 hours respectively.

It is generally accepted that lipogenesis induction requires a nitrogen starvation mechanism (Hegeset et al., 2019). To understand the relationship between de novo lipid accumulation and chemical modulators in the presence of nitrogen. However, no studies have showed the relationship between the addition of different concentrations of chemical modulators and lipid accumulation without nitrogen starvation. In the present disclosure, we attempted to induce lipid content with simultaneous higher biomass production and Omega-3-fatty acids (DHA) by optimization different combinations of external modulators without N-starvation condition.

Referring to FIG. 3, GM supplemented with citric acid (0.25-0.65%), malic acid (0.25-1%) and BAP (0.0005-0.0015%) ( ) enhanced lipid and DHA yield concomitantly with biomass production even in the presence of nitrogen. In nitrogen starved/limitation condition, lipid reached to 50-60% (of cell dry wt.) by compromising the biomass yield. The lipid yield has been significantly reduced in N-starvation/limitation condition as compared with lipid yield in the presence of nitrogen. The lipid content obtained was maximum 55-65% (of Cell dry weight) with higher biomass concentration (21-26 g/L) in supplemented medium, which were higher than that of lipid obtained in non-supplemented medium under N-replete/deplete condition. FIG. 3 depicts that the higher citric acid (1%) and BAP (0.0020%) (concentrations did not exhibit enhancement of lipid and DHA yield. To achieve efficient lipid accumulation in microbes, continuous supply of acetyl-CoA and NADPH directly in the cytosol of the cell is necessary for fatty acid biosynthesis (Ren et al., 2009). Citric acid flux flow to cytocol converts to acetyl Co-A by ATP citrate lyase under nitrogen limited condition, which participates in fatty acid biosynthesis (Ren et al., 2009). The external addition of citric acid along with malic acid and BAP have increased the citrate flux and NADPH supply to cytocol which directly be converted into acetyl-CoA. The results indicated that the metabolic flux from TCA cycle to the fatty acids biosynthesis was promoted by the external addition of appropriate quantity of modulators without N-starvation.

Example 4

The Effect of Combination of Chemical Modulators in Different Ratios on Biomass and Lipid Productivity This example shows the effect of different ratios of chemical modulators in a mixture supplemented in production media comprising of crude glycerol as a substrate with growth components for the aerobic fermentative biomass and high value lipids production process. Various ratios were tested by permutations and combinations of chemical modulators, some of the effects of different ratios are given in this example and Table 2.

Batch experiments were carried out in a parallel bioreactor (Biojenik Engineering, Chennai, India) with 2 L of supplemented GM medium, inoculated 10% v/v with a 24-h seed culture grown in GM containing 6 g/L glycerol. The culture was kept at 35° C. and aerated with 0.75-1 v/v/min air; stirring was regulated in the range from 150 to 900 rpm to keep the Dissolve oxygen at 20%. The medium pH, incubation temperature, time and agitation were 5.3-9.5, 35° C., and 24 h respectively.

TABLE 2

Table 2 describes the effect of different ratios of chemical modulators on biomass and lipid yield

| Modulators Ratio (Citric:Malic:BAP) | Biomass (g/L) | Lipid (% of DCW) | DHA (% TFA) |
|---|---|---|---|
| 0.54:0.45:0.001 | 23.69 | 43.5 | 17 |
| 0.499:0.499:0.0004 | 24.3 | 45.4 | 18.2 |
| 0.4:0.58:0.002 | 28.6 | 57.4 | 30.4 |

TABLE 2-continued

Table 2 describes the effect of different ratios of chemical modulators on biomass and lipid yield

| Modulators Ratio (Citric:Malic:BAP) | Biomass (g/L) | Lipid (% of DCW) | DHA (% TFA) |
|---|---|---|---|
| 0.642:0.35:0.001 | 22.868 | 45.28 | 23 |
| 0.734:0.26:0.001 | 19.225 | 51.87 | 18 |
| control | 20.56 | 42 | 17.8 |

Table 2 exhibits the effect of different ratios of chemical modulators on lipid, biomass and DHA enhancement. High ratio of malic acid and low citric acid concentrations in presence of some amount of BAP in a mixture exhibited concomitant enhancement of biomass along high value lipid. Other ratios of citric:malic:BAP did not increase overall productivities. They either enhanced biomass or lipid and or DHA. The high value lipids along with biomass has been increased with specific percentage of mixture of chemical modulators in medium ranging from 0.01% to 2% of total growth medium. The overall yield was improved. It was assumed that the presence of high malic acid than citric acid in a mixture increased the flux of malate in mitochondria where malate converted to citrate by citrate: malate antiporter that permitted the continual supply of acetyl COA.

Example 5

The Combination Effect of Mixture of Modulator in a Unique Ratio in Nitrogen Excess Media on the Enhancement of Lipid and Omega-3 Fatty Acid Concentrations In this embodiment the effect of modulators addition in production medium for the continuous simultaneous production of lipid, omega-3-fatty acids, and biomass. Production medium mainly comprising of glycerol as a substrate with all growth components and supplemented with modulators in the ratio of 0.4:0.58:0.002(citricacid:malicacid:BAP) as inducer for enhancement of lipid, omega-3-fatty acid along with biomass without nitrogen starvation. An experiment was designed to assess whether high cell density achievable by growth on supplemented media could be harnessed for higher overall lipid productivity by switching the specific ratio of modulators in mixture in the initial growth phase in single reactor without giving any N-stress.

Inoculum of selected strain of *Schizochytrium* sp. (MTCC 5980) was prepared in GM media as discussed in example 2 and incubated at 35° C., 200 rpm. 10% of 24 old inoculum was added in 2 L or 5 L or 10 L reactors half filled with modified medium having nitrogen source. Fermenter without supplemented media was kept as control. Culture was aerated with micro spargers or with normal drilled pipe spargers. Culture was agitated with Ruston or pitch blade or marine impellers at 100-900 rpm maintain dissolved oxygen (DO) at 10% to 50% or more with combination of air and oxygen supply. Sample was taken regularly at the interval of 6 to 12 h to determine nutrient sequestration, biomass production and lipid production and DHA production. Reactor pH was in the range of 5.3-9.5 and was not controlled during the continuous process.

Stepwise optimization strategy was followed to develop continuous valorisation process for high value lipids production from any waste streams by development of continuous cultivation process in bioreactor to enhance biomass and lipid production rate. Two stainless steel tubes were installed in 2 L bioreactor for continuous media feeding and continuous culture harvesting (through overflow tube) by peristaltic pump. Bioreactor was made continuous at 2nd day with sterile media with starting feeding rate of 600-1200 ml d$^{-1}$. Feeding rate was gradually increased using unsterile media until culture started washing out to achieve maximum dilution and growth rate. Feeding was continued for next 10 days at higher dilution rate and media level was maintained across the cultivation period.

Effluent liquid streams were measured via HPLC with refractive index detector (RID) detection. Growth was monitored via OD600 and gravimetrically. Conversion of OD to dry cell weight was via ratios determined in our laboratory. Total lipids were quantified using a modified version of a lipid extraction protocol adapted from U.S. Pat. No. 9,890, 402 B2 using gas chromatography-flame ionization detector (GCFID).

FIG. 4 exhibits the lipid productivity with specific ratio of media composition switch. In this experiment, specific ratios of mixture of modulators in presence of excess nitrogen exhibited enhancement in lipid, biomass and DHA yield much higher than that of the experiment conducted in same condition without supplementation of modulators. Please refer to FIG. 4a, the specific productivity of lipid and omega-3-fatty acids is about two-four times that achieved on control fermentor without supplemented media in the presence of nitrogen. On the other hand, much higher cell densities can be supported by switching to specific ratio of modulators in mixture. The maximum biomass and lipid productivity obtained was 88 g/L/d and 55 g/L/day respectively. The above yield was also better than the yield obtained by organisms in normal fermentations reported in previous literature studies.

Referring to FIG. 4b, without supplementation in media, nutrient sequestration rate was also less when compared with supplemented medium. At higher dilution, residual nitrate was more that led to a significant decline of lipid productivity. It was assumed that the presence of nitrogen down regulated the formation of lipid body membranes. We hypothesized that this might be due to low supply of acetyl-CoA and reducing power in the form of NADPH. Successful transition from carbon source to lipids in the presence of nitrogen without decline in cell mass and that also maintained the biosynthetic capacity of cells was achieved in a steady state when the continuous supply of supplemented medium was provided. Based on the performance of selected isolate in presence of specific ratio of mixture of modulators in this experiment, the biomass, lipid, and omega-3-fatty acid yield were improved by maximum 2.5-3.5-fold as compared to normal fermentation condition without modulators supplementation in the media.

Referring to Table 3, The specific productivity of lipid enriched with omega-3-fatty acids is about two which achieved on control fermentor without supplemented chemical modulators. On the other hand, much higher cell densities can be supported by switching to specific concentrations of chemical modulators in a steady state. The maximum biomass, lipid and DHA productivity obtained was 70 g/L/d, 45 g/L/day and 15 g/L/day, respectively. The above yield was also better than the yield obtained by other *Thraustochytrium* organisms in normal fermentations with and without chemical modulators reported in previous literature studies.

TABLE 3

Comparison of present invention to previous studies

| Strains | Fermentation mode | Growth medium | Biomass (g/L/d) | Lipid (g/L/d) | DHA (g/L/d) | Reference |
|---|---|---|---|---|---|---|
| *Schizochytrium* sp. (MTCC 5980) | Continuous | Minimal media + citric acid + BAP + Malic acid | 60-70 | 40-45 | 10-15 | Present |
|  |  | Minimal media (control) | 55-60 | 20-25 | 5 |  |
| *Schizochytrium* sp. ATCC 790 | Continuous | Complex medium without chemical modulators | 8.88 | — | 4.08 | Kujawska et al., 2021 |
| *Schyzochytrium limacinum* SR21. | Batch (6 days) | Complex medium + citric acid | 3 | 2.07 | 0.315 | Patil et al., 2015 |
|  |  | Complex medum + malic acid | 2.91 | 1.73 | 0.228 |  |
| *Aurantiochytrium* sp. YLH70 | Batch (120 h) | Complex medum + BAP | 4 | 2.11 | 0.92 | Yu et al., 2016 |
| *Aurantiochytrium* sp. ZJWZ-7 | Batch (120 h) | Complex medium + malic acid | 1.6 | — | 0.332 | Wang et al., 2019 |

REFERENCES AS PER TABLE 3

Wang Qiuzhen et al., 2019. Culturable Diversity and Lipid Production Profile of Labyrinthulomycete Protists Isolated from Coastal Mangrove Habitats of China. *Mar. Drugs* 2019, 17(5), 268

Patil et AL., 2015. Improved synthesis of Docosahexaenoic acid (DHA) using *Schyzochytrium limacinum SR*21 and sustainable media. *Chemical Engineering Journal* (2015), doi: http://dx.doi.org/10.1016/j.cej.2015.01.050

Yu X J, et al. 2016. Metabolomics analysis reveals 6-benzylaminopurine as a stimulator for improving lipid and DHA accumulation of *Aurantiochytrium* sp. J Chem Technol Biotechnol. 91(4):1199-207.

Kujawska et al. 2021. Cultivation Method Effect on *Schizochytrium* sp. Biomass Growth and Docosahexaenoic Acid (DHA) Production with the Use of Waste Glycerol as a Source of Organic Carbon. Energies. 14, 2952. https://doi.org/10.3390/en14102952

We claim:

1. A media supplement composition for enhancing production of omega-3-fatty acids from a carbon substrate, the media supplement composition comprising:
    a mixture of modulators,
    wherein the mixture of modulators comprises 0.25-0.65% citric acid, 0.25-1% malic acid, and 0.0005-0.0015% benzyl adenine purines.

2. The media supplement composition as claimed in claim 1, wherein the mixture of modulators comprises 0.1-10 g/L of citric acid, 0.1-12 g/L of malic acid, and 1-15 mg/L of benzyl adenine purines.

3. The media supplement composition as claimed in claim 1, wherein the mixture of modulators comprises citric acid, malic acid, and benzyl adenine purines in a ratio of 0.4:0.58:0.002.

4. A method for enhancing production of omega-3-fatty acids from a carbon substrate, the method comprising:
    adding a media supplement composition to a growth medium having the carbon substrate to form a supplemented growth medium; and
    culturing *Schizochytrium* sp. (MTCC 5980) in the supplemented growth medium,
    wherein the media supplement composition comprises 0.01-2% of a mixture of modulators of a total weight of the growth medium, wherein the mixture of modulators comprises 0.25-0.65% citric acid, 0.25-1% malic acid, and 0.0005-0.0015% benzyl adenine purines.

5. The method as claimed in claim 4, wherein the low-cost-carbon substrate is glycerol.

6. The method as claimed in claim 4, wherein the method is carried out in absence of a nitrogen stress induction.

7. The method as claimed in claim 4, wherein the mixture of modulators comprises 0.1-10 g/L of citric acid, 0.1-12 g/L of malic acid, and 1-15 mg/L of benzyl adenine purines.

8. The method as claimed in claim 4, wherein the mixture of modulators comprises citric acid, malic acid, and benzyl adenine purines in a ratio of 0.4:0.58:0.002.

9. The method as claimed in claim 4, wherein the growth medium and the supplemented growth medium have a pH in a range of 5.3-9.5.

10. The method as claimed in claim 4, wherein *Schizochytrium* sp. (MTCC 5980) is cultured at a temperature in a range of 30-35° C. for 24 hours.

11. The method as claimed in claim 4, wherein the method is carried out in a single reactor, and wherein the single reactor is a continuous reactor.

* * * * *